(12) United States Patent
Lacoux

(10) Patent No.: US 8,729,243 B2
(45) Date of Patent: May 20, 2014

(54) METHOD FOR PREPARING POLYBIOTINYLATED COMPOUNDS

(75) Inventor: Xavier Lacoux, Dommartin (FR)

(73) Assignee: bioMérieux, Marcy l'Etoile (FR)

( * ) Notice: Subject to any disclaimer, the term of this patent is extended or adjusted under 35 U.S.C. 154(b) by 21 days.

(21) Appl. No.: 13/521,085

(22) PCT Filed: Jan. 11, 2011

(86) PCT No.: PCT/FR2011/050048
§ 371 (c)(1),
(2), (4) Date: Jul. 9, 2012

(87) PCT Pub. No.: WO2011/086321
PCT Pub. Date: Jul. 21, 2011

(65) Prior Publication Data
US 2012/0330028 A1    Dec. 27, 2012

(30) Foreign Application Priority Data

Jan. 12, 2010 (FR) ...................... 10 50174

(51) Int. Cl.
*C07K 1/00*       (2006.01)
*C07K 14/00*     (2006.01)
*C07K 16/00*     (2006.01)
*C07K 17/00*     (2006.01)

(52) U.S. Cl.
USPC ...................................................... 530/409

(58) Field of Classification Search
None
See application file for complete search history.

(56) References Cited

U.S. PATENT DOCUMENTS

2005/0215771 A1* 9/2005 Lacoux .................... 530/395
2006/0228325 A1* 10/2006 Wilbur et al. ............. 424/78.3

FOREIGN PATENT DOCUMENTS

| EP | 07741191 | 5/1997 |
| WO | WO-96/03650 A1 | 2/1996 |
| WO | WO-00/72802 A2 | 12/2000 |
| WO | WO-01/02861 A1 | 1/2001 |
| WO | WO-03072546 A1 | 9/2003 |
| WO | WO-2005/034909 A2 | 4/2005 |

OTHER PUBLICATIONS

Westerlind U, et al., "Ligands of the asialoglycoprotein receptor for targeted gene delivery, part 1: Synthesis of and binding studies with biotinylated cluster glycosides containing N-acetylgalactosamine" Glycoconjugate Jorunal 21, 227-241, 2004.

Ludemann, Susanna, "International Search Report" for PCT/FR2011/050048 as mailed Jun. 14, 2011, 3 pages.

* cited by examiner

*Primary Examiner* — Marcela M Cordero Garcia
*Assistant Examiner* — Kaipeen Yang
(74) *Attorney, Agent, or Firm* — Winstead PC

(57) ABSTRACT

The present invention relates to a novel method for preparing compounds having the formula (I),

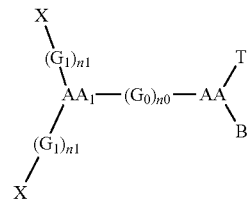

where
  X is biotin or

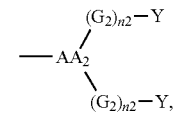

Y being biotin or

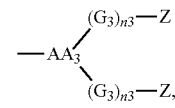

Z being biotin or

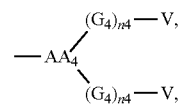

V being biotin or

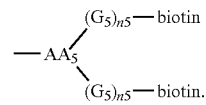

It also relates to compounds having the formula (I) and their use in clinical and industrial diagnosis.

9 Claims, 7 Drawing Sheets

METHOD FOR PREPARING POLYBIOTINYLATED COMPOUNDS

Figure 1:
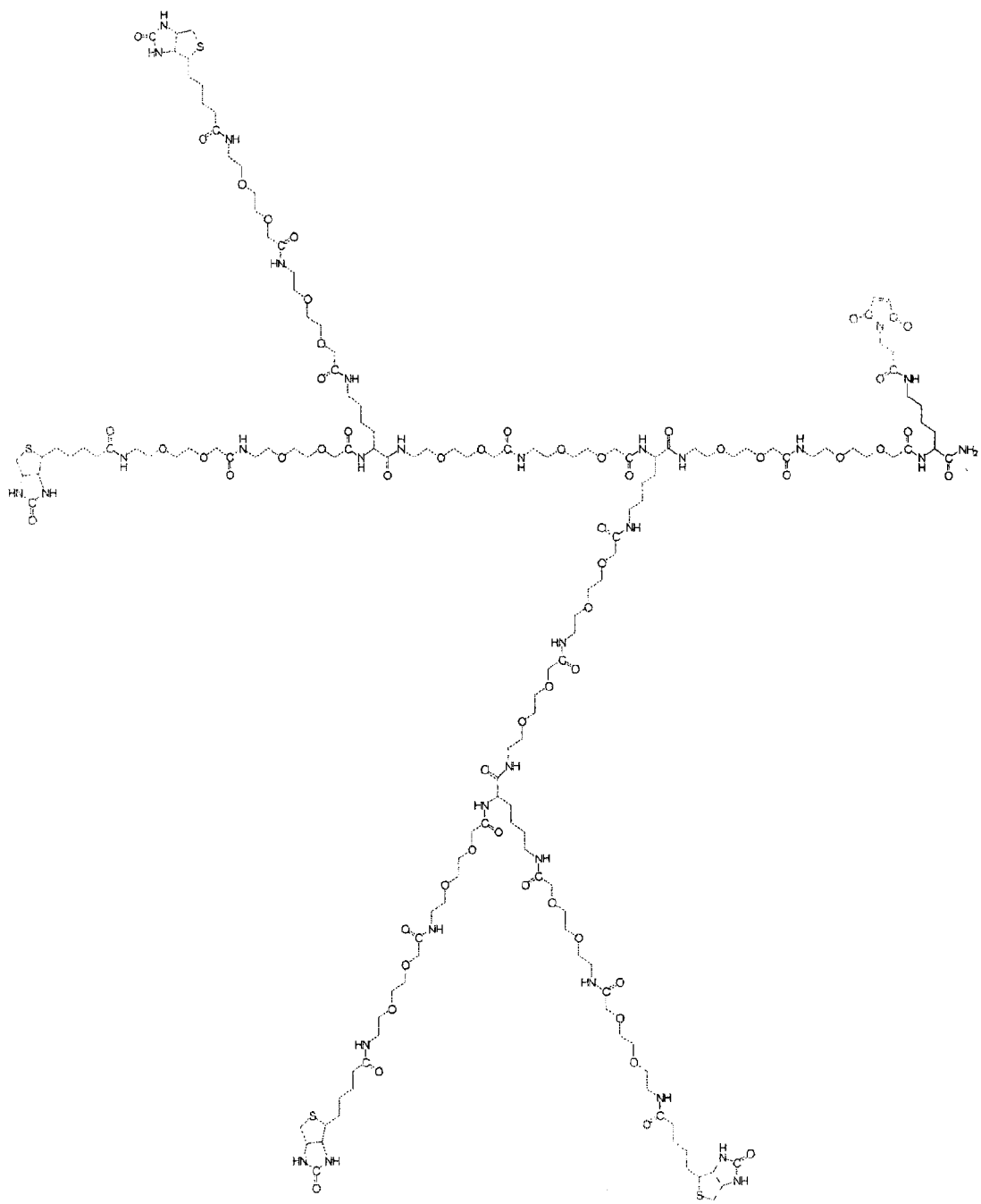

The present invention relates to the field of diagnosis. In particular, it relates to a method for producing polybiotinylated dendrimer compounds useful for signal amplification, in particular during the detection of an analyte in a diagnostic test.

Probes which allow the detection of analytes such as proteins and nucleic acids are widely used and are tools of choice for in vitro and in vivo diagnosis. However, it may be difficult to detect these analytes because they are not always present in sufficiently large quantities. A detection amplification system is therefore necessary.

Several techniques have been developed for detecting analytes in insufficient quantities. These techniques involve either increasing the quantity of analyte, for example with PCR or NASBA techniques, or amplifying the detection, for example by using structures having multiple markers.

Thus, patent application EP0774119A describes conjugates having multiple markers comprising a polymer support having a maximum of 100 monomer units, which contains 1 to 10 molecules of haptene and 1 to 10 marker groups, and also the preparation of these conjugates by solid-phase synthesis (a) by introducing, at predetermined positions of the support, monomer derivatives which are coupled covalently to haptene molecules and/or marker groups and/or (b) by coupling haptene molecules and/or marker groups to reactive groups of the support, after the synthesis.

Dendrimers are clearly defined macromolecules which have multiple branches and which terminate in multiple peripheral functional groups. One of the advantages of dendrimers, due to the fact that they have multiple functional groups, is that they can be used as stable coupling agents, as described in patent application WO03/72546 filed by the Applicant. Another advantage also resides in the fact that they are structures with multiple markers because their peripheral functional groups can be used to bind multiple markers such as biotin, fluorophores or a combination thereof. Thus, patent application WO01/02861 describes dendrimers bound on the one hand to 1 to 1200 probes and on the other hand to 1 to 1200 markers. These dendrimers are used for signal amplification.

Other polybiotinylated dendrimers have also been described in patent application WO00/72802.

However, conventional methods for preparing dendrimers have the drawbacks that the dendrimers are synthesised in liquid phase, which is more complex and more lengthy than in solid phase. Furthermore, some methods produce non-neutral and non-polarised dendrimers.

The Applicant has now surprisingly developed a novel method for preparing polybiotinylated dendrimer compounds which make it possible to overcome the drawbacks of the prior art methods in the sense that they allow the reproducible and controlled preparation of the biotinylated compounds which are:

- water-soluble although electrically neutral,
- polarised thanks to a separate and precise spatial distribution of their functions, including the biotin function, and
- synthesised in solid phase.

Thus, a first object of the present invention is a method for preparing a compound having the formula (I):

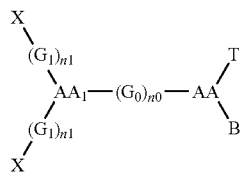

(I)

where

X is biotin or

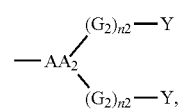

Y is biotin or

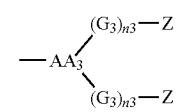

Z is biotin or

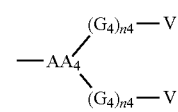

V is biotin or

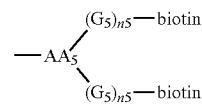

B is $NH_2$ or H,

AA is a trifunctional molecule derivative when B is $NH_2$ or a bifunctional molecule derivative when B is H, $AA_1$ to $AA_5$ are each independently a trifunctional molecule derivative, $G_0$ to $G_5$ are each independently an arm comprising at least one ($-CH_2-CH_2-O$) unit, $n_0$ to $n_5$ are each independently a whole number between 1 and 8 and T is an antiligand or a reactive group for fixation to an antiligand, said antiligand being capable of reacting with a ligand, characterised in that it comprises the steps consisting in:

(i) grafting $n_0$ compounds having the formula $W''_0-G_0-OH$, where $W''_0$ is an amine protecting group, $n_0$ and $G_0$ being such as defined above, to a compound having the formula (II):

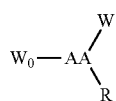
(II)

where R is a prefunctionalised resin, W and $W_0$ are different from one another and represent an amine protecting group, W being different from $W''_0$, and AA is such as defined above, to obtain a compound having the formula (III):

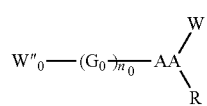
(III)

(ii) coupling a compound having a formula (IV):

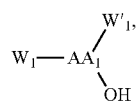
(IV)

where $W_1$ and $W'_1$ are amine protecting groups that are identical to or different from one another and from the $W_0$ and $W''_0$ groups, but different from W, and $AA_1$ is such as defined above, with the compound having the formula (III) to obtain a compound having the formula (V):

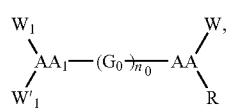
(V)

(iii) grafting $2n_1$ compounds having the formula $W''_1$-$G_1$-OH, where $W''_1$ is an amine protecting group, identical to or different from one another and from the other protecting groups used in this method, but different from W, $G_1$ and $n_1$ being such as defined above, onto the compound obtained in step (ii) to obtain a compound having the formula (VI):

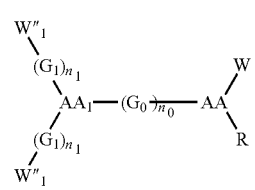
(VI)

(iv) when X in the formula (I) is biotin, passing directly to step (v); if not, when X in the formula (I) is not biotin, repeating the steps (ii) and (iii) with $2^{p-1}$ compounds having the formula (VII):

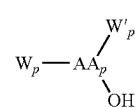
(VII)

and $2^p n_p$ times the compound having the formula $W''_p$-$G_p$-OH, where p is a whole number between 2 and 5, and $W_p$, $W'p$, $W''p$ are amine protecting groups that are identical to or different from one another and from the other protecting groups used in this method, but different from W, and $AA_p$ is a trifunctional molecule, according to the following sequence:

1 time when Y is biotin, p then being equal to 2

2 times when Y is not biotin and Z is biotin, p then being equal to 2 then to 3, 3 times when Y and Z are not biotin and V is biotin, p then being equal to 2, 3 then 4, and 4 times when Y, Z and V are not biotin, p then being equal to 2, 3, 4 then 5, (v) deprotecting the compound thus obtained at the $W''_1$ or $W''_p$ group, p being between 2 and 5, and coupling with biotin, (vi) deprotecting, at the W group, the compound thus poly-biotinylated and coupling with an antiligand or a reactive group for fixation to an antiligand (T) and (vii) cutting the compound thus obtained from the resin (R) to obtain a compound having the formula (I).

A further object of the invention relates to the compounds having the formula (I) in which:

X is biotin or

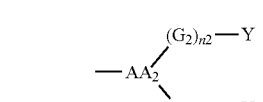

Y is biotin or

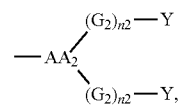

Z is biotin or

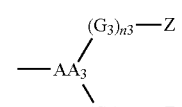

V is biotin or

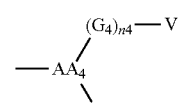

B is $NH_2$ or H,

AA is a trifunctional molecule derivative when B is $NH_2$ or a bifunctional molecule derivative when B is H, $AA_1$ to $AA_4$ are each independently a trifunctional molecule derivative, $G_0$ to $G_5$ are each independently an arm comprising at least one (—$CH_2$—$CH_2$—O—) unit, $n_0$ to $n_5$ are each independently a whole number between 1 and 8 and T is a maleimide group, a carboxylic acid group or an antiligand.

The invention finally relates to the use of the compounds that can be obtained by the method described above, for signal amplification in a diagnostic test.

The method of the invention therefore serves to prepare biotinylated compounds in a reproducible and controlled manner. Furthermore, said compounds obtained are highly soluble even without electrical charge due to the presence of the substituents $G_0$ to $G_5$. Their particular dendrimer structure allows polarisation of the molecule, of which the steric hindrance is controlled, thereby allowing a better presentation of the biotins and hence the amplification of the signal, in particular when it is used in a diagnostic application, due to the presence of 2 to 32 biotins. The compounds obtained are then particularly useful for the detection of an analyte in a very small quantity.

The dendrimer structure of the compounds obtained by the method of the invention is obtained thanks to the use of derivatives of trifunctional or bifunctional molecules.

Bifunctional molecule is understood to mean any molecule comprising at least one trivalent or tetravalent atom carrying two functions enabling them to react with two molecules. These functions are selected from $NH_2$ and COOH. These bifunctional molecules may then comprise two identical or different functions, that is to say two $NH_2$ functions, two COOH functions or even one COOH function and one $NH_2$ function. As a non-limiting example of bifunctional molecules, mention can be made of bifunctional diamines such as ethylenediamine and 4,7,10-trioxamidecanediamine.

Derivative of bifunctional molecule is understood to mean the bifunctional molecule in which each of the two functions is in a bonding engagement with another chemical entity. Thus, the bifunctional molecule derivative consists of the skeleton of the bifunctional molecule in which each $NH_2$ function has lost a hydrogen atom and each COOH function has lost a hydroxyl (OH) radical. Thus, for example, when the bifunctional molecule derivative is ethylenediamine, having the formula $H_2N$—$CH_2$—$CH_2$—$NH_2$, the ethylenediamine derivative is —HN—$CH_2$—$CH_2$—NH—.

When the substituent AA is a bifunctional molecule derivative, B is H in the formula (I).

Trifunctional molecule is understood to mean any molecule comprising at least one trivalent or tetravalent atom carrying three functions enabling them to react with three molecules. These functions are selected from $NH_2$ and COOH. These trifunctional molecules may then comprise three identical or different functions, that is to say, three $NH_2$ functions, two $NH_2$ functions and one COOH function, two COOH functions and one $NH_2$ function or even three COOH functions. As a non-limiting example of trifunctional molecules, mention can be made of lysine, diaminobutanoic acid, diaminopropanoic acid, L-ornithine and derivatives thereof.

Trifunctional molecule derivative is understood to mean the trifunctional molecule in which each of the three functions is in a bonding engagement with another chemical entity. Thus, the trifunctional molecule derivative consists of the skeleton of the trifunctional molecule in which each $NH_2$ function has lost a hydrogen atom and each COOH function has lost a hydroxyl (OH) radical. Thus, for example, when the trifunctional molecule derivative is lysine, having the formula $H_2N$—$(CH_2)_4$—$CH(NH_2)$—COOH, the lysine derivative is —HN—$(CH_2)_4$—CH(NH—)—CO—.

When the substituent AA is a trifunctional molecule derivative, B is $NH_2$ in the formula (I).

According to a preferred embodiment, the compounds in the method of the invention have one of the following features:

the substituents $AA_1$ and $AA_2$, if applicable $AA_3$, $AA_4$ and $AA_5$, are identical and are preferably a lysine derivative, the substituent AA is a lysine derivative and B is $NH_2$.

The solubility of the compounds obtained with the method of the invention derives from the nature of the spacer arms $G_0$ to $G_5$ used because they comprise at least one (—$CH_2$—$CH_2$—O—) unit. Preferably, the compounds of the invention comprise one to six (—$CH_2$—$CH_2$—O—) units, even more preferably one to four (—$CH_2$—$CH_2$—O—) units. As non-limiting examples of such spacer arms, mention can be made of pentaoxaoctadecanoyl, tetraoxapentadecanoyl, trioxadodecanoyl, trioxamidecanoyl, dioxaoctanoyl, oxapentoyl and hexaoxaheneicosanoyl and derivatives thereof.

According to an embodiment, the compounds in the method of the invention have one of the following features:

the substituents $G_0$, $G_1$, if applicable $G_2$, $G_3$, $G_4$ and $G_5$ are identical and preferably have the formula (—NH—$CH_2$—$CH_2$—O—$CH_2$—$CH_2$—O—$CH_2$—CO—).

the whole numbers $n_0$, $n_1$, if applicable $n_2$, $n_3$, $n_4$ and $n_5$, are identical and are preferably equal to 2 or 3.

In the compounds prepared according to the method of the invention, T is an antiligand or a reactive group for fixation to an antiligand.

Antiligand is understood to mean any molecule capable of bonding with a ligand. Examples of ligand/anti-ligand pairs are well known to the person skilled in the art, which is the case for example with the following pairs: haptene/antibody, antigen/antibody, peptide/antibody, sugar/lectin, polynucleotide/polynucleotide complementary.

Reactive groups for fixation to an antiligand are widely known to the person skilled in the art. Non-limiting examples of such groups are the maleimide, carboxylic acid, thiol, amine, alkoxyamine, hydrazine, azido, alkyne, aldehyde groups.

The compounds obtained by the method according to the invention allow the amplification of the detection signal in a diagnostic test due to the presence of several biotins, according to Table 1 below:

TABLE 1

| Number of biotins | X | Y | Z | V |
|---|---|---|---|---|
| 2 | Biotin | NA | NA | NA |
| 4 | —$AA_2$(($G_2)_{n2}$—Y)(($G_2)_{n2}$—Y) | biotin | NA | NA |
| 8 | —$AA_2$(($G_2)_{n2}$—Y)(($G_2)_{n2}$—Y) | —$AA_3$(($G_3)_{n3}$—Z)(($G_3)_{n3}$—Z) | biotin | NA |
| 16 | —$AA_2$(($G_2)_{n2}$—Y)(($G_2)_{n2}$—Y) | —$AA_3$(($G_3)_{n3}$—Z)(($G_3)_{n3}$—Z) | —$AA_4$(($G_4)_{n4}$—V)(($G_4)_{n4}$—V) | biotin |

TABLE 1-continued

| Number of biotins | X | Y | Z | V |
|---|---|---|---|---|

NA: not applicable

According to a particular embodiment of the invention, X is

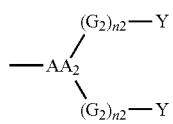

and Y is biotin.

The grafting and coupling steps of the method according to the invention are steps conventionally used by the person skilled in the art in the field of solid-phase synthesis of the peptide synthesis type. These steps can be implemented manually or even in an automated manner on commercial synthesisers such as the ABI 431 A and ABI433A synthesiser.

The reagents used during these steps are known to the person skilled in the art and are described for example in Chemical Approaches to the Synthesis of Peptides & Proteins, Paul Lloyd Williams, Fernando Albericio, Ernest Giralt, CRC Press.

Thus, the compounds having the formula (II) in which R is a prefunctionalised resin and AA is a bifunctional molecule derivative are available from Novabiochem. By way of example, mention can be made of:

the compound Universal NovaTag resin, reference 04-12-3910 having the formula:

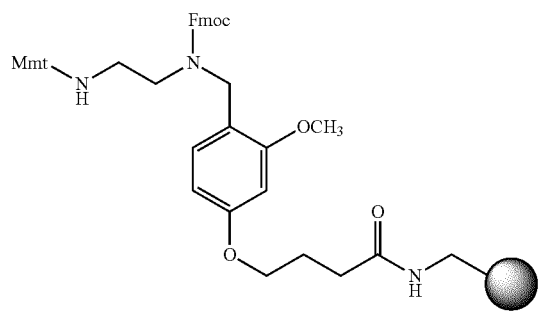

the compound Universal PEG NovaTag resin, reference 04-12-3911 having the formula:

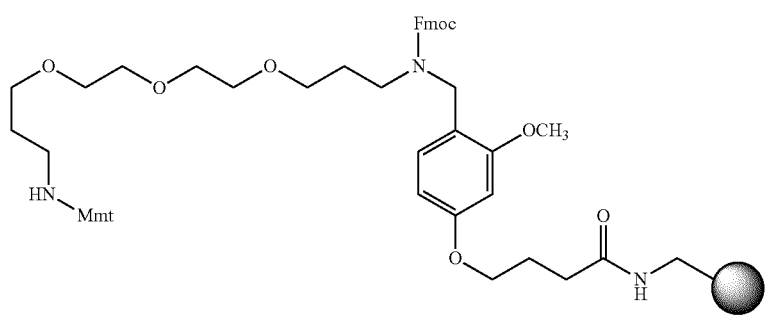

When AA is a trifunctional molecule in the compounds having formula (II), the latter can be obtained by coupling a compound having the formula (II')

in which $W_o$ and W are such as defined above, onto a solid amine phase having the formula (II") $W_{r'}$—R in which R is

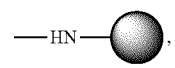

and $W_{r'}$ is an amine protecting group identical to or different to $W_o$ and W.

An example of a solid amine phase comprises the resin RINK-amide-MHBA from Novabiochem (Reference 01-64-0037).

The steps of deprotection and separation of the polybiotinylated compound of the resin R are widely known to the person skilled in the art and are described for example in Chemical Approaches to the Synthesis of Peptides & Proteins (supra).

Amine protecting groups are also widely known to the person skilled in the art and, as non-limiting examples, mention can be made of t-butyloxycarbonyl (Boc), benzyloxycarbonyl, 9-fluorenylmethoxycarbonyl (Fmoc) or methoxytrityl (Mmt). Any protecting group can be employed in the method according to the invention insofar as W is different from the other protecting groups used.

According to an embodiment, the compounds in the method according to the invention have one of the following features:

the W group is methoxytrityl, the $W_1$ and $W'_1$ groups are identical and, if applicable, $W_2$ and $W'_2$ are identical, $W_3$ and $W'_3$ are identical, $W_4$ and $W'_4$ are identical and $W_5$ and $W'_5$ are identical, the $W_1$, $W'_1$ groups and, if applicable, $W_2$, $W'_2$, $W_3$, $W'_3$, $W_4$ and $W'_4$, $W_5$ and $W'_5$ are fluorenylmethoxycarbonyl groups.

The method according to the invention serves to prepare novel polybiotinylated dendrimer compounds having the formula (I)

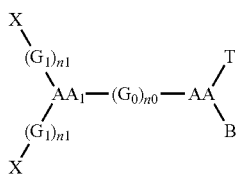
(I)

where
X is biotin or

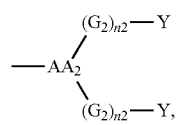

Y is biotin or

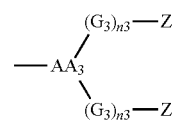

Z is biotin or

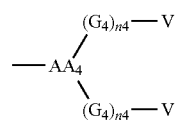

V is biotin or

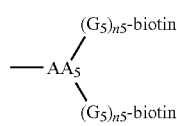

B is $NH_2$ or H,

AA is a trifunctional molecule derivative when B is $NH_2$ or a bifunctional molecule derivative when B is H, $AA_1$ to $AA_4$ are each independently a trifunctional molecule derivative, $G_0$ to $G_5$ are each independently an arm comprising a ($-CH_2-CH_2-O-$) unit, $n_0$ to $n_5$ are each independently a whole number between 1 and 8 and T is a maleimide group, a carboxylic acid group or an antiligand.

According to a particular embodiment, the compounds of the invention comprise one of the following features:

the substituents $AA_1$ and $AA_2$, if applicable $AA_3$, $AA_4$ and $AA_5$, are identical and are preferably a lysine derivative, the substituents $G_0$, $G_1$, if applicable $G_2$, $G_3$, $G_4$ and Gs, are identical and preferably have the formula ($-NH-CH_2-CH_2-O-CH_2-CH_2-O-CH_2-CO-$), the whole numbers $n_0$, $n_1$, if applicable $n_2$, $n_3$, $n_4$ and $n_5$, are identical and are preferably equal to 2 or 3, X is

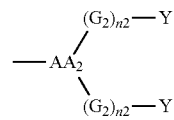

and Y is biotin,
AA is a lysine derivative and B is $NH_2$,
the antiligand is a Fab' fragment,
X is

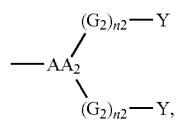

Y is biotin, AA, $AA_1$ and $AA_2$ are a lysine derivative, $G_0$, $G_1$ and $G_2$ have the formula ($-NH-CH_2-CH_2-O-CH_2-CH_2-O-CH_2-CO-$), $n_0$, $n_1$ and $n_2$ are equal to 2, B is $NH_2$ and T is an antiligand, preferably a Fab' fragment.

The compounds prepared by the method of the invention are particularly useful for signal amplification in in vitro diagnostic methods implying a recognition of a ligand/antiligand pair, the molecule to be diagnosed constituting the ligand, which thus constitutes another object of the invention.

In fact, the compounds of the invention directly possess an antiligand (substituent T) or are reacted with an antiligand which shall be fixed on said substituent T by methods well known to the person skilled in the art.

Examples of ligand/anti-ligand pairs are well known to the person skilled in the art, which is the case for example of the following pairs: haptene/antibody, antigen/antibody, peptide/antibody, sugar/lectin, polynucleotide/polynucleotide complementary.

In vitro diagnostic methods which can employ the conjugates of the invention are in particular immunological tests such as the sandwich methods like ELISA, IRMA and RIA, methods called competition methods and direct immune detection methods such as immunohistochemistry, immunocytochemistry, Western-blot and Dot-blot. All these methods are well known to the person skilled in the art.

Diagnostic methods employing compounds prepared according to the method of the invention are useful both in clinical diagnosis of diseases and in the diagnosis of products prepared in industry (industrial diagnosis) such as products intended for the agroprocessing industry and products intended for health care.

Diseases which can be diagnosed with the compounds of the invention are not limited and comprise all diseases revealed by the presence of a specific marker of the disease, such as the molecule of biological interest or analyte or ligand, for which a bonding partner exists. As non-limiting examples, mention can be made of viral diseases such as hepatitis and AIDS, and solid cancers such as breast, colon or prostate cancer.

The signal amplification is carried out by the use of a marker molecule capable of directly or indirectly generating a detectable signal. A non-limiting list of these markers consists of:

enzymes which produce a signal that is detectable for example by colourimetry, fluorescence, luminescence, such as horseradish peroxidase, alkaline phosphatase, β-galactosidase, glucose-6-phosphate dehydrogenase, chromophores such as fluorescent, luminescent, dye compounds, radioactive molecules such as $^{32}$P, $^{35}$S or $^{125}$I, and fluorescent molecules such as Alexa or phycocyanines, with the understanding that these markers will be modified to be bound to a bonding partner with biotin such as streptavidin. This type of modification is well known to the person skilled in the art.

According to the type of marking used, the person skilled in the art will add reagents allowing visualisation of the marking.

Figure 2:
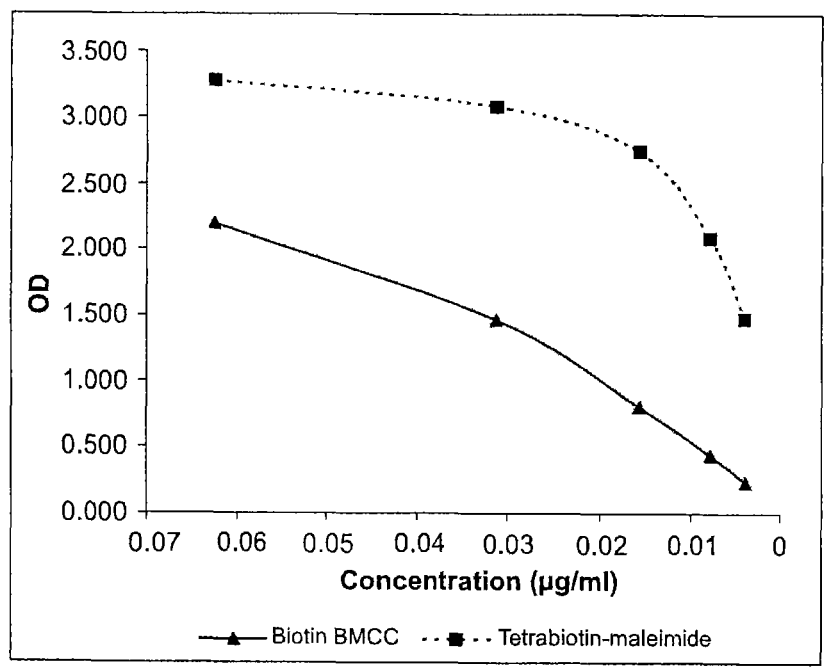
Figure 3:
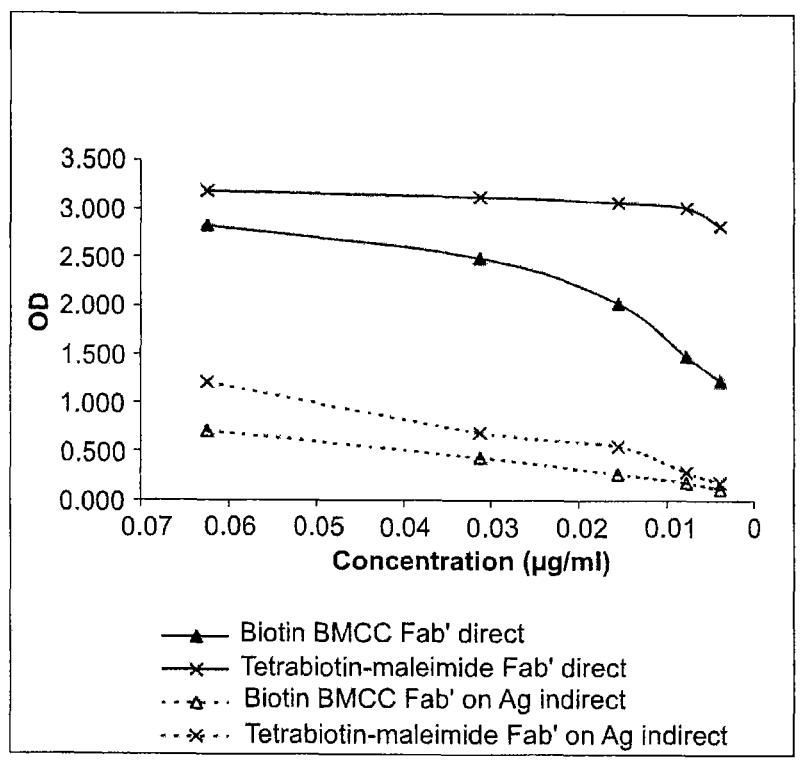
Figure 4:
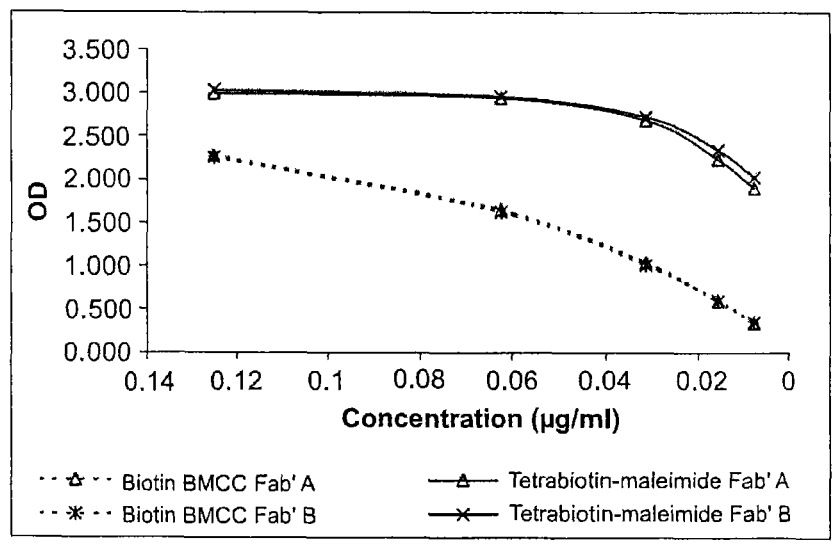
Figure 5:
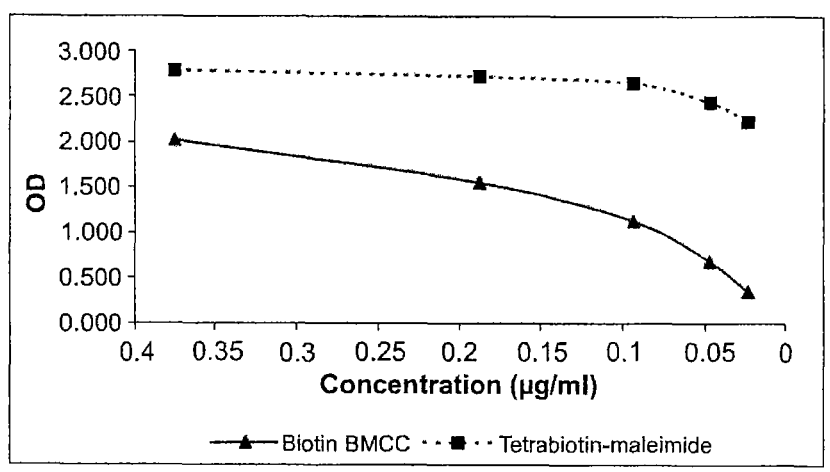
Figure 6:
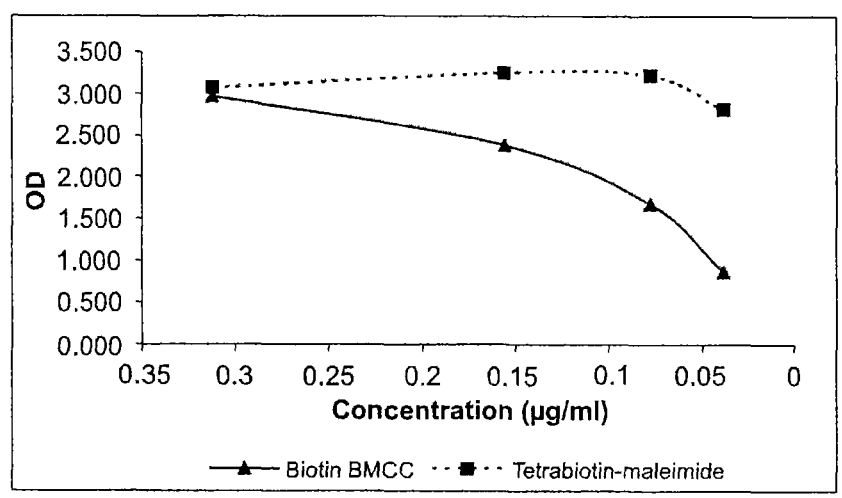
Figure 7:
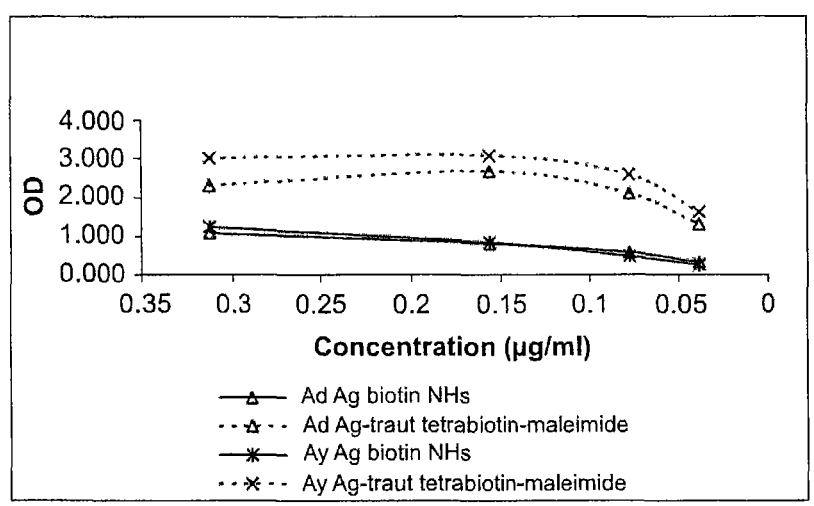
Figure 8:
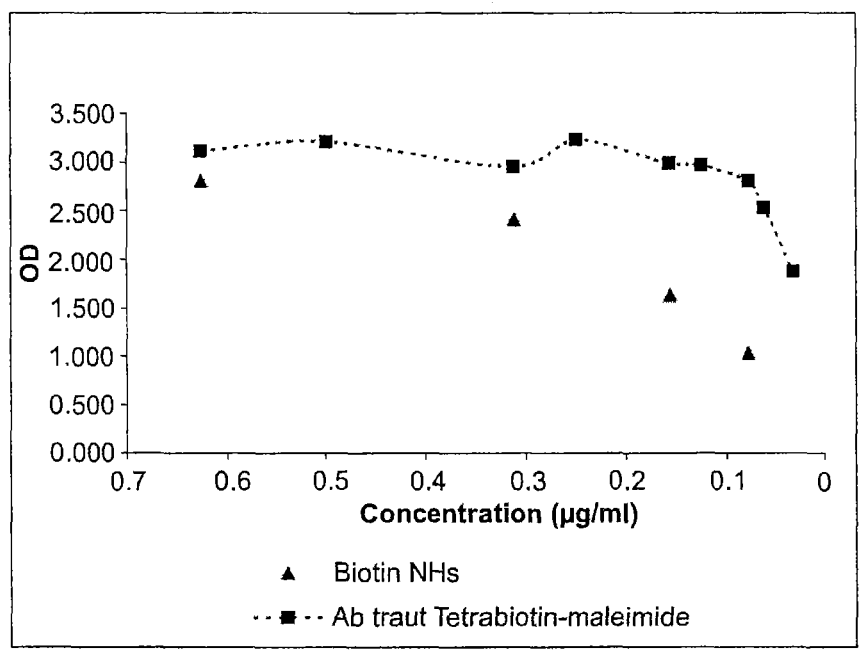

The invention will be better understood with the help of the following examples which are provided for illustration and are non-limiting, and with reference to FIGS. 1 to 8, in which:

FIG. 1 corresponds to the developed formula of a compound having 4 biotins according to an embodiment, FIG. 2 is a graphic representation giving the OD results of a direct ELISA test of an anti-*Listeria monocytogenes* Fab' conjugate that is monobiotinylated (by biotin BMCC) or tetrabiotinylated (by a compound according to an embodiment of the invention), fixed to the bottom of a microplate, according to its concentration, FIG. 3 is a graphic representation giving the OD results of a direct ELISA test of an anti-Salmonella Fab' conjugate that is monobiotinylated (by biotin BMCC) or tetrabiotinylated (by a compound according to an embodiment of the invention), fixed to the bottom of a microplate, according to their concentration, and also an indirect ELISA test with these same conjugates, but detected by means of *Salmonella* antigens, FIG. 4 is a graphic representation giving the OD results of a direct ELISA test of anti-HIV Fab' conjugate that is monobiotinylated (by biotin BMCC) or tetrabiotinylated (by a compound according to an embodiment of the invention), fixed to the bottom of a microplate, according to its concentration, FIG. 5 is a graphic representation giving the OD results of a direct ELISA test of an anti-Kallikrein Fab' conjugate that is monobiotinylated (by biotin BMCC) or tetrabiotinylated (by a compound according to an embodiment of the invention), fixed to the bottom of a microplate, according to its concentration, FIG. 6 is a graphic representation giving the OD results of a direct ELISA test of an antigen gp160 conjugate reduced to DTT that is monobiotinylated (by biotin BMCC) or tetrabiotinylated (by a compound according to an embodiment of the invention), fixed to the bottom of a microplate, according to its concentration, FIG. 7 is a graphic representation giving the OD results of a direct ELISA test of surface antigen conjugates of hepatitis B that are monobiotinylated (by biotin NHs) or tetrabiotinylated (by a compound according to an embodiment of the invention), fixed to the bottom of a microplate, according to their concentration, and FIG. 8 is a graphic representation giving the OD results of a direct ELISA test of an anti-Salmonella antibody conjugate that is monobiotinylated (by biotin NHs) or tetrabiotinylated (by a compound according to an embodiment of the invention), fixed to the bottom of a microplate, according to its concentration.

EXAMPLE 1

Preparation of a Compound Having the Formula (I) with 4 Biotins ($AA=AA_1=AA_2$=lysine derivative;
B is $NH_2$;
$G_0=G_1=G_2$=(—NH—$CH_2$—$CH_2$—O—$CH_2$—$CH_2$—O—$CH_2$—CO—)=Ado;
$n_0=n_1=n_2=2$
T=maleimide

X=

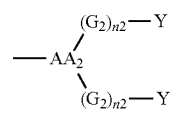

Y=biotin)

About 132 μmoles of Fmoc-RINK-MBHA (Novabiochem) resin were placed in a reactor of a 433A automatic synthesiser (Applied Biosystems) equipped with a UV detector. Cartridges were also prepared each containing synthons at the rate of 1 mmole per cartridge:

Fmoc-Lys(Mmt)-OH, 640.8 mg (Novabiochem)
Fmoc-Lys(Fmoc)-OH, 590.7 mg (Novabiochem)
Fmoc-Ado-OH, 385.4 mg (or Fmoc-8-amino-3,6-dioxaoctanoic acid, Polypeptide)
N-maleoyl-βalanine, 169.1 mg (FLUKA)
Biotin, MW 244.3 (SIGMA) previously taken up in 0.5 M solution in DMSO (ALDRICH), or 2 ml of solution per cartridge The following raw materials were used:
N-methyl-pyrrolidone or NMP (Applied Biosystems)
Dichloromethane or DCM (Applied biosystems)
Piperidine (ALDRICH)
Acetic anhydride (FLUKA)
Methanol (MERCK)
Solution of di-isopropylethylamine or DIEA (ALDRICH), 2 M in NMP above
Solution of hexafluorophosphate benzotriazolyl tetramethyluronium or HBTU (Novabiochem) in equivalence with N-hydroxybenzotriazole (SENN) the whole in solution at about 0.45 M in N,N-dimethylformamide or DMF (ALDRICH)
Solution containing 1% trifluoroacetic acid or TFA (ACROS) and 2.5% tri-isopropylsilane or TIS (FLUKA) in the same DCM as above.

By default, 2 cartridges of each synthon were provided to be incorporated in order to work in Conditional Double Coupling mode.

The programming of the synthesiser is based on a succession of cycles, themselves divided into modules, the modules being a series of primary functions on the programmable logic controller. The programmes of the supplier were used as the basis, and were adapted for the preparation of the following example:

The following molecules were used:
A: recovery of the amino acid powder cartridge
B: deprotection of the Fmoc N-terminal group with piperidine
C: capping or masking of unreacted amines with acetic anhydride
D: rinsings of the resin with NMP
E: activation and transfer of the amino acid solution to the resin
F: coupling with stirring
G: deprotection of the monomethoxytrityl of the side chain of the 1$^{st}$ lysine
I: intermittent stirring of the reactor for 30 minutes
a: conditional module for recovery of the cartridge, rinsing of the resin and activation/transfer to the reactor
b: conditional module of additional deprotections with piperidine
c: rinsing of the resin with DCM
d: other module of rinsing of the resin with NMP
f: conditional module of long coupling with stirring
i: conditional module of ejection of unused cartridge The synthesiser was programmed according to the cycles as indicated in Table 2 below:

TABLE 2

| Cycle | AA | Name | Modules |
|---|---|---|---|
| 1 | Fmoc-Lys(Mmt)-OH | Conditional double coupling and capping | BbADEFfiafCd |
| 2 | Fmoc-Ado-OH | Conditional double coupling and capping | BbADEFfiafCd |
| 3 | Fmoc-Ado-OH | Conditional double coupling and capping | BbADEFfiafCd |
| 4 | Fmoc-Lys(Fmoc)-OH | Conditional double coupling and capping | BbADEFfiafCd |
| 5 | Fmoc-Ado-OH | Long condition double coupling and capping | BbADEFfIiafICd |
| 6 | Fmoc-Ado-OH | Long conditional double coupling and capping | BbADEFfIiafICd |
| 7 | Fmoc-Lys(Fmoc)-OH | Long conditional double coupling and capping | BbADEFfIiafICd |
| 8 | Fmoc-Ado-OH | Very long conditional double coupling and capping | BbADEFfIIiafIICd |
| 9 | Fmoc-Ado-OH | Very long conditional double coupling and capping | BbADEFfIIiafIICd |
| 10 | Biotin | Very long conditional double coupling and capping | BbADEFfIIiafIICd |
| 11 | N-maleoyl-βalanine | Long double coupling Lys(Mmt) deprotection and capping | GcADEFIAdEFfICd |
| 12 | None | Resin washings with NMP and DCM | Dcc |

During the deprotections of the Fmoc group, the apparatus performs a test. According to the result obtained, the programme makes a single or double coupling (use respectively only 1 or the 2 cartridges provided).

1.1. Coupling $1^{st}$ lysine (AA)

The resin is deprotected and Fmoc-Lys(Mmt)-OH (II') is coupled as follows (cycle 1: the apparatus uses only 1 or the 2 cartridges of Fmoc-Lys(Mmt)-OH amino acid according to the result of the conditional test):

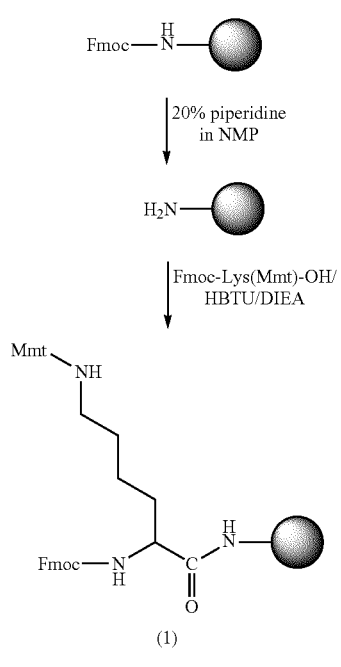

(1) or (II"): also represented by

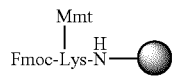

(1)

1.2. Construction of the Skeleton:
This consists in the alternation of:
a) grafting the hydrophilic spacer arm Ado$_2$
b) coupling the branching synthon=Fmoc-Lys(Fmoc)-OH
Based on (1) above
i) grafting of Hydrophilic Spacer Arm Ado$_2$ (Step a)
(cycles 2 and 3: the apparatus uses 1 or the 2 cartridges of Fmoc-Ado-OH amino acid in each cycle according to the result of the conditional tests)

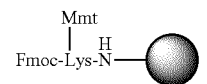

(1)

1) 20% piperidine in NMP
2) Fmoc-Ado-OH/HBTU/DIEA

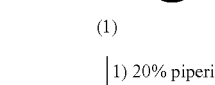

(2)

1) 20% piperidine in NMP
2) Fmoc-Ado-OH/HBTU/DIEA

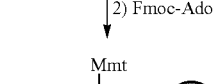

(3)

ii) Branching by Fmoc-Lys(Fmoc)-OH (Step b)
(cycle 4: the apparatus uses only 1 or the 2 cartridges of Fmoc-Lys(Fmoc)-OH amino acid according to the result of the conditional test)
Based on (3)

```
            Mmt
             | H
Fmoc-Ado-Ado-Lys-N──●
```
(3)

↓ 1) 20% piperidine in NMP
  2) Fmoc-Lys(Fmoc)-OH/HBTU/DIEA

```
    Fmoc        Mmt
     |           | H
Fmoc-Lys-Ado-Ado-Lys-N──●
```
(4)

iii) Repetition of Steps a), b) then a to Terminate the Skeleton cycles 5 and 6: the apparatus uses 1 or the 2 cartridges of each Fmoc-Ado-OH amino acid according to the result of the conditional tests:

```
    Fmoc        Mmt
     |           | H
Fmoc-Lys-Ado-Ado-Lys-N──●
```
(4)

↓ 1) 20% piperidine in NMP
  2) Fmoc-Ado-OH/HBTU/DIEA

```
        Fmoc
         |
         Ado            Mmt
         |               | H
Fmoc-Ado-Lys-Ado-Ado-Lys-N──●
```
(5)

↓ 1) 20% piperidine in NMP
  2) Fmoc-Ado-OH/HBTU/DIEA

```
            Fmoc
             |
             Ado
             |
             Ado                Mmt
             |                   | H
Fmoc-Ado-Ado-Lys-Ado-Ado-Lys-N──●
```
(6)

cycle 7: the apparatus uses only 1 or the 2 cartridges of Fmoc-Lys(Fmoc)-OH amino acid according to the result of the conditional test:

```
                Fmoc
                 |
                 Ado
                 |
                 Ado                Mmt
                 |                   | H
Fmoc-Ado-Ado-Lys-Ado-Ado-Lys-N──●
```
(6)

↓ 1) 20% piperidine in NMP
  2) Fmoc-Lys(Fmoc)-OH/HBTU/DIEA

```
                Fmoc
                 |
                Fmoc-Lys
                 |
                 Ado
                 |
                 Ado                Mmt
                 |                   | H
Fmoc-Lys-Ado-Ado-Lys-Ado-Ado-Lys-N──●
                 |
                Fmoc
```
(7)

cycles 8 and 9: the apparatus uses only 1 or the 2 cartridges of Fmoc-Ado-OH amino acid according to the result of the conditional tests:

↓ 1) 20% piperidine in NMP
  2) Fmoc-Ado-OH/HBTU/DIEA

```
                    Fmoc
                     |
                Fmoc-Ado-Lys
                     |
                     Ado
                     |
                     Ado                Mmt
                     |                   | H
Fmoc-Ado-Lys-Ado-Ado-Lys-Ado-Ado-Lys-N──●
                     |
                     Ado
                     |
                    Fmoc
```
(8)

↓ 1) 20% piperidine in NMP
  2) Fmoc-Ado-OH/HBTU/DIEA

```
                        Fmoc
                         |
                         Ado
                         |
                         Ado
                         |
                    Fmoc-Ado-Ado-Lys
                         |
                         Ado
                         |
                         Ado                Mmt
                         |                   | H
Fmoc-Ado-Ado-Lys-Ado-Ado-Lys-Ado-Ado-Lys-N──●
                         |
                         Ado
                         |
                         Ado
                         |
                        Fmoc
```
(9)

1.3. Coupling of a Biotin to Each End of the 4 Branches:

(cycle 10: the apparatus uses only 1 or the 2 cartridges of biotin according to the result of the conditional test)

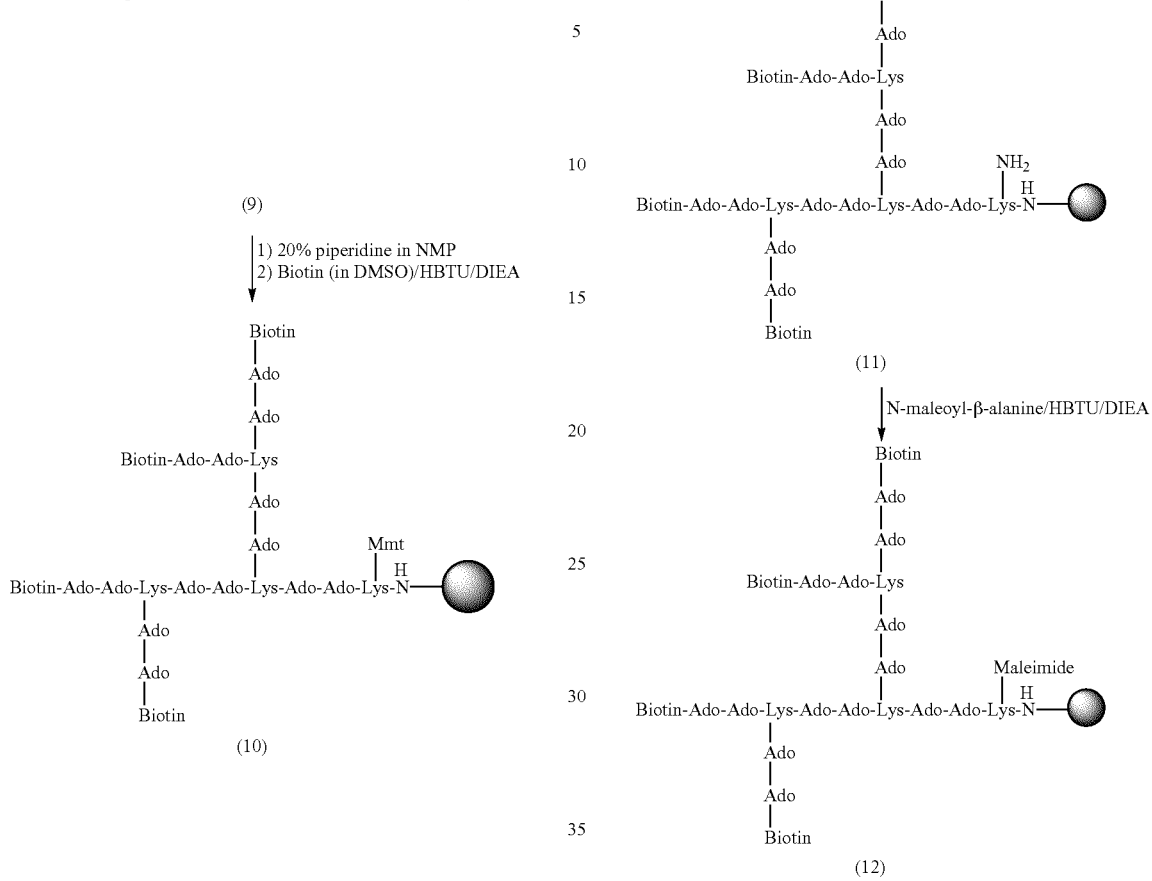

1.4. Deprotection of Mmt and Grafting of Maleimide:

(cycle 11: this time, the programme uses the 2 cartridges of N-maleoyl-β-alanine—no conditional test).

The protecting group Mmt is cut selectively by repeated action of a solution of DCM (dichloromethane) containing 1.5% TFA (trifluoroacetic acid) and 1.5% TIS (tri-isopropyl-silane). The amine of the side chain of the lysine inserted in step 1) is thus liberated for its coupling with an acidic form of maleimide, N-maleoyl-β-alanine.

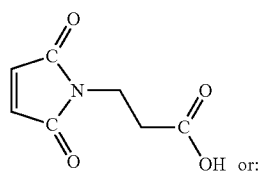

1.5. Cleavage

After synthesis, the resin is dried by nitrogen blanketing. It is transferred to a 20 ml plastic syringe comprising a sinter and contacted with 10 ml of a TFA/water (95/5) solution with stirring for 1 hour 30 minutes at ambient temperature. The cleavage solution is then collected by filtration (via the sinter of the syringe) in a glass flask. The resin is rinsed with about 5 ml of TFA, and then 3 times with about 5 ml of DCM. All these volumes are added to the flask. The raw cleavage mixture is evaporated under reduced pressure with a rotary evaporator of which the bath is at ambient temperature for a few tens of minutes. An oily orange-coloured residue is finally obtained.

This product is taken up in a few milliliters of deionised water for analyses and purification.

The aliquot, rediluted in deionised water, is analysed by HPLC and mass spectrometry coupled to HPLC.

BECKMAN analytical HPLC with VYDAC $C_{18}$ reverse-phase chromatography column 5.4 mm in diameter by 250 mm in length, with the eluants A=water containing 0.1% TFA and B=mixture of acetonitrile or ACN with water (95/5 respectively) containing 0.1% TFA. The flow rate is 1 ml/min. Sample injection is followed by a gradient from 0 to 80% acetonitrile in 30 minutes. Under these conditions, after the dead volume peak at about 3 minutes, the tetrabiotinylated molecule/maleimide exits at around 15 minutes. LC/MS analysis (HPLC and THERMO ELECTRON mass detector) is used to identify the compound anticipated with a recalculated molecular weight of 3617.7 g/mole (theoretical 3618.26)

The remainder of the raw mixture is purified in at least three equivalent volumes by injection in BECKMAN semi-preparative HPLC on a VYDAC $C_{18}$ reverse-phase column 20 mm in diameter by 250 mm in length, at the rate of 22 ml/min. The eluants A and B are identical to those used in analytical HPLC. Typical purification programme: after injection, rest for 10 minutes at 5% eluant B; then passage from 5 to 23% eluant B in 1 minute; then purification gradient from 23 to 31% B in 30 minutes. Under these conditions, the purification fractions are taken on arrival of the bulk of the desired product, from about 21 minutes, at the rate of 0.33 minute per tube, until about minutes (about 25 tubes). An aliquot of each tube is analysed in isocratic mode by analytical HPLC (same conditions as above except isocrate of 26% eluant B for 10 minutes).

The purest fractions are collected in a glass flask and the solution is then freeze-dried. After freeze-drying and weighing, the lyophilisate is taken up in deionised water at 1 mg/ml according to the weighing. This stock solution is distributed in brown glass bottles at the level of 1 to a few milliliters per bottle. The bottles are then again freeze-dried and plugged under inert atmosphere of 700 millibar argon.

An aliquot is used to perform the final analysis by HPLC (BECKMAN, identical conditions to the 1$^{st}$ analysis with gradient above), LC/MS (conditions identical to above) and analysis of amino acids according to the supplier's procedure on the Agilent 1100 system series with detection by fluorescence.

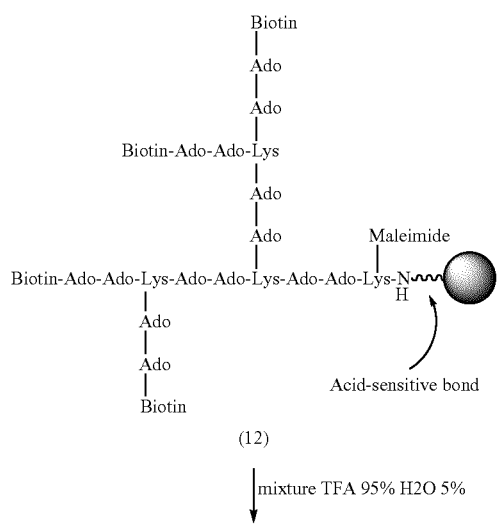

(12)

↓ mixture TFA 95% H2O 5%

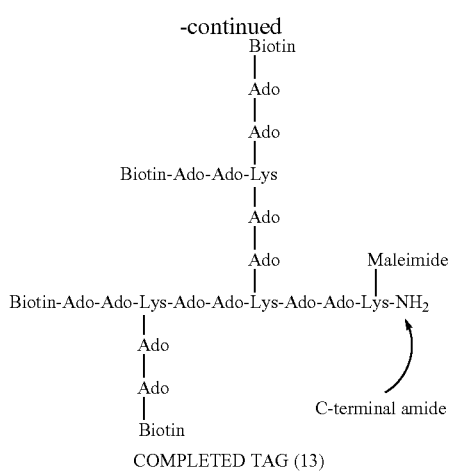

COMPLETED TAG (13)

The tetrabiotinylated compound (13) thus obtained has the developed formula as described in FIG. 1.

EXAMPLE 2

Preparation of a Compound Having the Formula (I) with 4 Biotins (AA=AA$_1$=AA$_2$=lysine derivative;
B is NH$_2$;
G$_0$=G$_1$=G$_2$=(—NH—CH$_2$—CH$_2$—O—CH$_2$—CH$_2$—O—CH$_2$—CO—)=Ado;
n$_0$=n$_1$=n$_2$=3
T=maleimide
X=

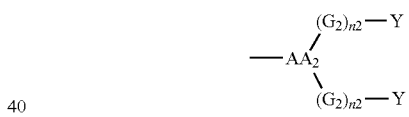

Y=biotin)

In this example, the same reagents were used as those described in example 1, with the exception of the resin: about 148 micromolecules of H-RINK-ChemMatrix resin (MATRIX Innovation) in free amine form without Fmoc group were placed in the reactor of the ABI433A synthesiser.

2.1 Coupling 1$^{st}$ lysine (AA):

Unlike in example 1, Fmoc-Lys(Mmt)-OH was coupled manually. The resin is already in amine form and does not require deprotection. 137 micromoles of Fmoc-Lys(Mmt)-OH taken up in solution in NMP were then sent manually to the reactor with 1 equivalent of HBTU/HOBt coupling agent. The reagents finally have a volume of about 6 ml. The coupling reaction is then started up by sending 0.5 ml of the same solution of DIEA 2 M/NMP into the reactor. The resin is in slight excess. The reaction is carried out for 2 hours at laboratory temperature with intermittent vortex. The synthesis is then resumed in fully automated mode following the programme indicated in Table 3 below:

TABLE 3

| Cycle | AA | Name | Modules |
|---|---|---|---|
| 1 | Fmoc-Lys(Mmt)-OH | End of coupling and masking of residual amines of the resin | IIDCCDD |

TABLE 3-continued

| Cycle | AA | Name | Modules |
|---|---|---|---|
| 2 | Fmoc-Ado-OH | Conditional double coupling and capping | BbADEFfiafCd |
| 3 | Fmoc-Ado-OH | Conditional double coupling and capping | BbADEFfiafCd |
| 4 | Fmoc-Ado-OH | Conditional double coupling and capping | BbADEFfiafCd |
| 5 | Fmoc-Lys(Fmoc)-OH | Conditional double coupling and capping | BbADEFfiafCd |
| 6 | Fmoc-Ado-OH | Long conditional double coupling and capping | BbADEFfIIiafIICd |
| 7 | Fmoc-Ado-OH | Long conditional double coupling and capping | BbADEFfIIiafIICd |
| 8 | Fmoc-Ado-OH | Long conditional double coupling and capping | BbADEFfIIiafIICd |
| 9 | Fmoc-Lys(Fmoc)-OH | Long conditional double coupling and capping | BbADEFfIIiafIICd |
| 9 | Fmoc-Ado-OH | Very long conditional double coupling and capping | BbADEFfIIIIiafIIIICd |
| 10 | Fmoc-Ado-OH | Very long conditional double coupling and capping | BbADEFfIIIIiafIIIICd |
| 11 | Fmoc-Ado-OH | Very long conditional double coupling and capping | BbADEFfIIIIiafIIIICd |
| 12 | Biotin | Very long conditional double coupling and capping | BbADEFfIIIIiafIIIICd |
| 13 | N-maleoyl-βalanine | Deprotection Lys(Mmt) long double coupling and capping | GcADEFIAdEFfICd |
| 14 | None | Resin washing with NMP and DCM | Dcc |

After the first cycle of this programme, the same type of structure is obtained as compound (I) of example 1.

2.2 Construction of the Skeleton

The procedure described in section 1.2 step i) was repeated, except that this step i) is repeated three times and in consequence, 3 Fmoc-Ado-OH (and no longer 2) are coupled in succession to achieve the following structure (step 2.2.i)):

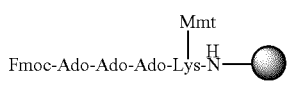

(14)

The branching was then carried out identically to step 1.2 ii) by coupling Fmoc-Lys(Fmoc)-OH to obtain (step 2.2.ii)):

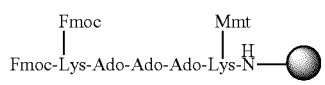

(15)

Steps 2.2 i) and 2.2 ii) were then repeated identically to achieve the following molecule with two branches:

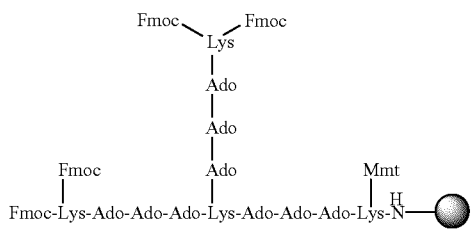

(16)

Steps 2.2 i) and 2.2 ii) above were then repeated identically again to achieve the intermediate molecule with four branches protected by "Fmoc":

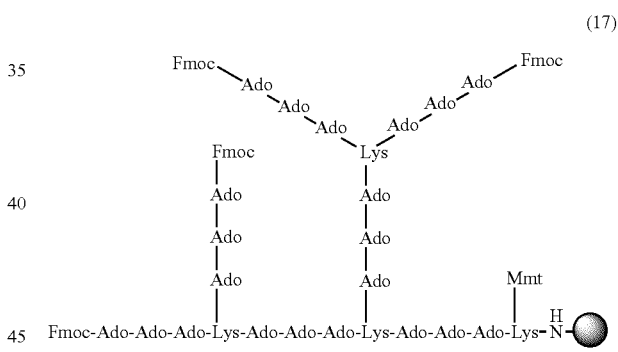

(17)

The procedure described in sections 1.3, 1.4 was then followed to achieve the tetrabiotinylated molecule with maleimide:

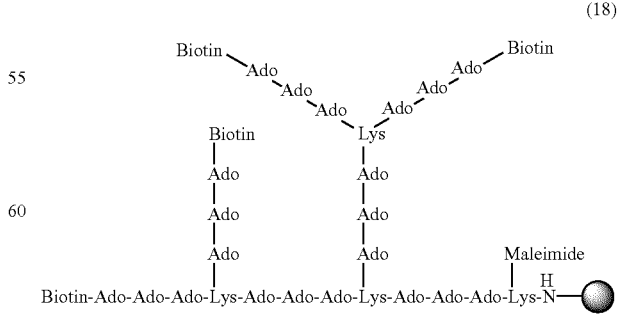

(18)

The cleavage of the molecule from its support, the analysis and purification, were then carried out under conditions similar to those of example 1. With analytical HPLC (identical experimental conditions) the exit of the tetrabiotinylated molecules/maleimide was observed with arms of "3 Ado" at around 15 minutes. The LC/MS analysis (identical conditions) confirms the presence of the anticipated compound with a recalculated molecular weight of 4634 g/mole (theoretical 4634.37). This molecule was purified under identical conditions to example 1, except that the purification gradient consists this time of a passage from 22 to 32% of eluant B, also in 30 minutes.

As in example 1, the purest fractions are collected and the mixture is freeze-dried. After this, the lyophilisate is weighed and taken up in water (soluble) and distributed in fractions of 1 to a few milliliters, which are freeze-dried in turn and then plugged under inert atmosphere of 700 millibar argon.

As in example 1, an aliquot is used to perform the identical final analyses.

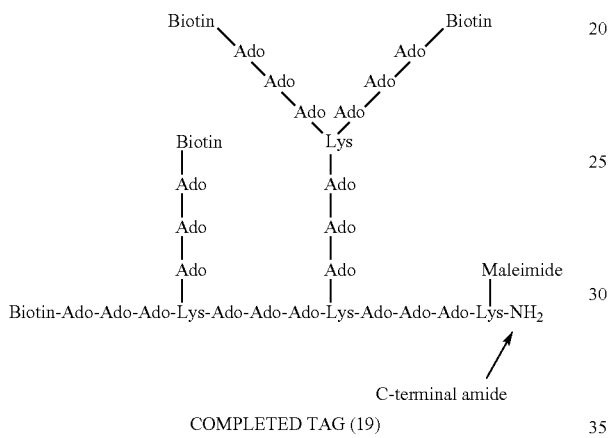

COMPLETED TAG (19)

EXAMPLE 3

Preparation of a Compound Having the Formula (I) with 8 Biotins ($AA=AA_1=AA_2=AA_3$=lysine derivative;

B is $NH_2$;

$G_0=G_1=G_2=G_3=(-NH-CH_2-CH_2-O-CH_2-CH_2-O-CH_2-CO-)$=Ado;

$n_0=n_1=n_2=3$

T=maleimide

Y=

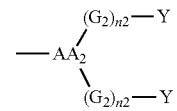

Z=biotin

To obtain this structure with eight branches, the method use in example 1 was repeated, with a few differences. The programme used on the ABI433A synthesiser is the one shown in Table 4 below:

TABLE 4

| Cycle | AA | Name | Modules |
|---|---|---|---|
| 1 | Fmoc-Lys(Mmt)-OH | Single coupling in low stoechiometry and masking of residual amines of the resin | BbDgFfIIIIIICCd |
| 2 | Fmoc-Ado-OH | Conditional double coupling and capping | BbADEFfiafCd |
| 3 | Fmoc-Ado-OH | Conditional double coupling and capping | BbADEFfiafCd |
| 4 | Fmoc-Ado-OH | Conditional double coupling and capping | BbADEFfiafCd |
| 5 | Fmoc-Lys(Fmoc)-OH | Conditional double coupling and capping | BbADEFfiafCd |
| 6 | Fmoc-Ado-OH | Conditional double coupling and capping | BbADEFfiafCd |
| 7 | Fmoc-Ado-OH | Conditional double coupling and capping | BbADEFfiafCd |
| 8 | Fmoc-Ado-OH | Conditional double coupling and capping | BbADEFfiafCd |
| 9 | Fmoc-Lys(Fmoc)-OH | Conditional double coupling and capping | BbADEFfiafCd |
| 9 | Fmoc-Ado-OH | Long conditional double coupling and capping | BbADEFfIIiafIICd |

TABLE 4-continued

| Cycle | AA | Name | Modules |
|---|---|---|---|
| 10 | Fmoc-Ado-OH | Long conditional double coupling and capping | BbADEFfIIiafIICd |
| 11 | Fmoc-Ado-OH | Long conditional double coupling and capping | BbADEFfIIiafIICd |
| 12 | Fmoc-Lys(Fmoc)-OH | Long conditional double coupling and capping | BbADEFfIIiafIICd |
| 13 | Fmoc-Ado-OH | Long conditional double coupling and capping | BbADEFfIIIAdEFfIIICd |
| 14 | Fmoc-Ado-OH | Long conditional double coupling and capping | BbADEFfIIIAdEFfIIICd |
| 15 | Fmoc-Ado-OH | Long conditional double coupling and capping | BbADEFfIIIAdEFfIIICd |
| 16 | Biotin | Long conditional double coupling and capping | BbADEFfIIIAdEFfIIICd |
| 17 | N-maleoyl-βalanine | Deprotection Lys(Mmt) long double coupling and capping | GcADEFIAdEFfICd |
| 18 | None | Resin washings with NMP and DCM | Dcc |

The loading of 448 micromoles of resin (Fmoc-RINK-MBHA) is carried out automatically but with only 80 micromoles of Fmoc-Lys(Mmt)-OH to achieve the compound on resin (1) of example 1. The excess amine on the resin is masked by acetylation.

The synthesis then continues as an example 2, until the step for obtaining the structure (17).

From then on, steps 2.2 i) and 2.2 ii) of example 2 are repeated identically, to achieve the intermediate molecule with eight branches protected by "Fmoc" groups:

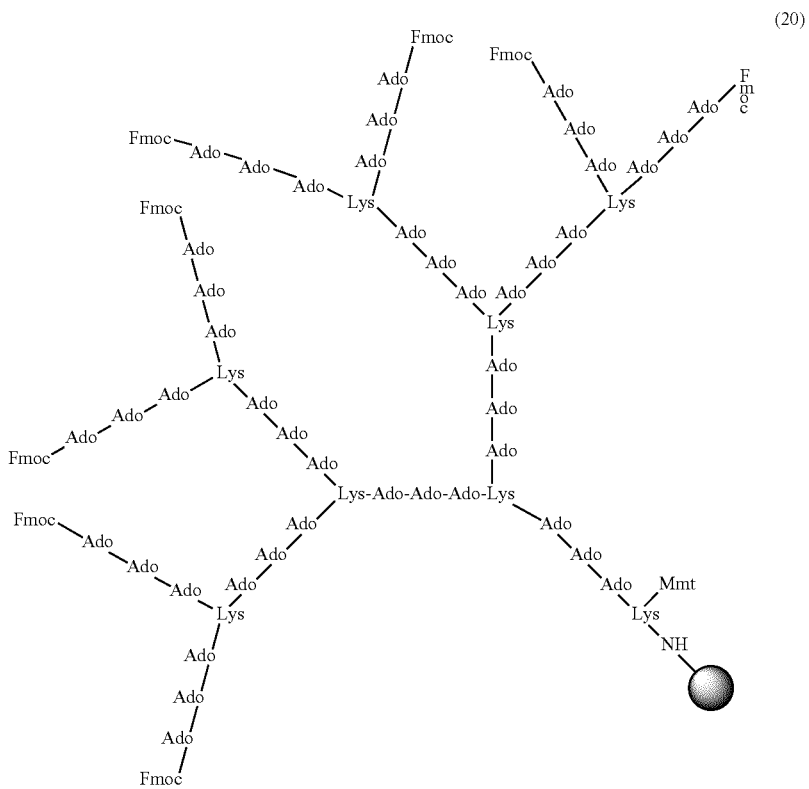

(20)

Then, as for example 1, identical steps to sections 1.3, 1.4 of example 1 were carried out, to achieve the octobiotinylated molecule with maleimide:

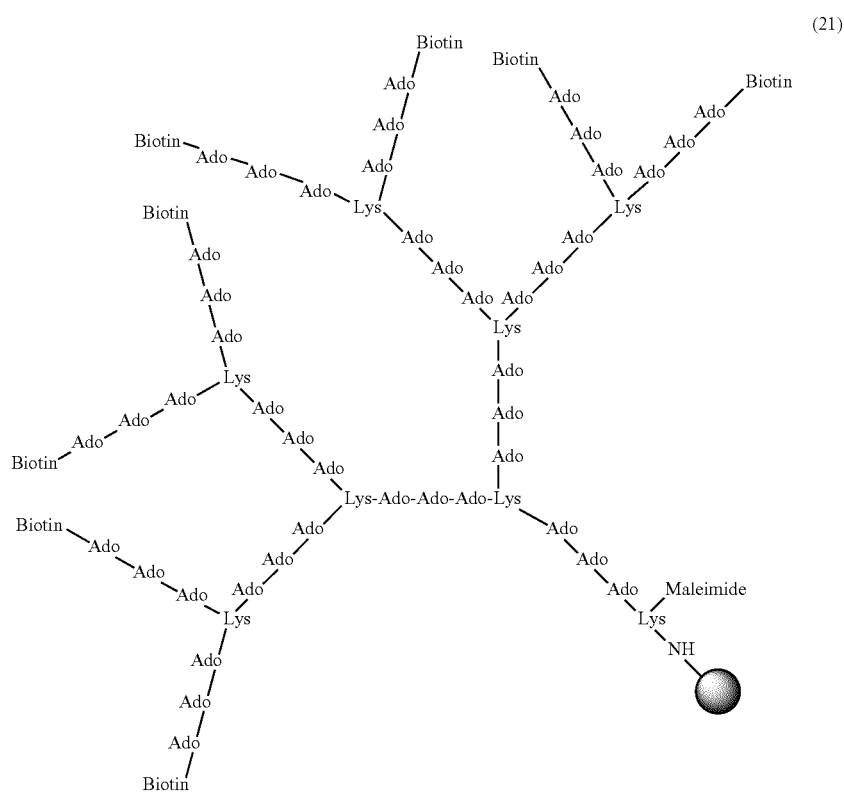

(21)

The cleavage of the molecule from its support is carried out under similar conditions to example 1.5, as well as the analysis and purification. In analytical HPLC (identical experimental conditions), the octobiotinylated molecule/maleimide with arms of 3 Ado exits in the form of a broad peak at around 16 minutes. The LC/MS analysis (identical conditions) confirms the presence of the anticipated compound with a recalculated molecular weight of 9535 g/mole (theoretical 9536.06). This molecule is purified under identical conditions to example 1, except that the purification gradient consists of a passage from 25 to 35% of eluant B in 30 minutes.

As in example 1, the purest fractions are collected and the mixture is freeze-dried. After this, the lyophilisate is weighed and taken up in water (soluble) and distributed in fractions of 1 to a few milliliters, which are freeze-dried in turn and then plugged under inert atmosphere of 700 millibar argon.

As in example 1, an aliquot is used to perform the identical final analyses.

The octobiotinylated molecule/maleimide with arms of "3 Ado" obtained is the following molecule (22):

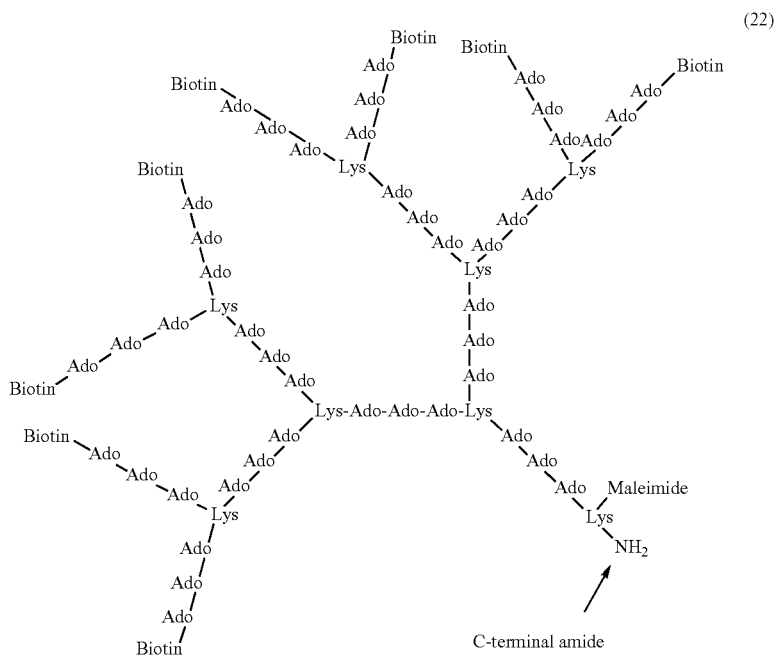

(22)

EXAMPLE 4

Coupling of SH Proteins with a Compound Having the Formula (I)

4.1. Context

The coupling of biotin on SH proteins (for example Fab' fragments, antigens reduced with DTT and proteins modified by Traut's reagent) is carried out conventionally by using biotin BMCC (Pierce ref 21900:1-Biotinamido-4{4'-(maleimidomethyl)cyclohexanecarboxamido]butane) with fixes to the free sulphydryl functions of the SH proteins. However, the small quantity of free sulphydryl functions does not allow fixation of a large number of biotins, so that when the biotin/SH protein conjugate is used for diagnosis, the detection signal is weak, which is representative of the presence of one biotin per conjugate. It is therefore important to enhance the signal.

The compounds of the invention serve to bond from 2 to 32 biotins and the Applicant has demonstrated that, against all expectations, they preserved a signal proportional to the number of biotins present, after coupling the SH proteins to the free sulphydryl radicals, despite their steric hindrance due to the large number of bonded biotins.

The coupling protocol is described in the following sections.

4.2. Reagents

The commercial reagents used are listed in Table 5.

TABLE 5

| Name | Supplier | References |
|---|---|---|
| Pepsin agarose | Sigma | P0609-50KU |
| 2 β mercapto ethanol | Thermo scientific | 35602 |
| Biotin BMCC | Thermo scientific | 21900 |

TABLE 5-continued

| Name | Supplier | References |
|---|---|---|
| DMSO | Merck | 1.02950.0500 |
| Iodoacetamide | Sigma | I6125 |
| Traut's reagent | Thermo scientific | 26101 |
| N-ethylmaleimide | Sigma | E-3876 |
| DTT | Sigma | D0632 |
| Biotin NHs | Roche | 11003933 |

Furthermore, the SH proteins used, obtained from bioMerieux, France, are the following:
Fab' fragments: anti-*Listeria monocytogenes* Fab' fragment, anti-antigen of the *Salmonella* wall, anti-p24 of HIV clone A and clone B and anti-human kallikrein 2;
Antigens used: gp160 of HIV, HBs Ad of HBV, HBs Ay of HBV
Antibodies: *Salmonella* wall anti-antigen antibody.
The antigens used for the indirect ELISA assay of the Fab' fragments of *Salmonella* were obtained after culture of *Salmonella bergedorf*, *typhimurium* and *enteritidis* strains in peptone medium for 24 h at 37° C., and then heating for 15 min at 100° C.

Finally, the compound having formula (I) prepared according to example 1 was used.

4.3. Coupling to Biotin BMCC and to the Compound of Example 1 on Fab'

The conjugates were obtained by coupling as follows:
Fab' fragment obtained by pepsic digestion, then reduction with 2βME, adjusted to 2 mg/ml after purification on Superdex 200 prep grade, in PO$_4$50 mM+NaCl 150 mM+EDTA (4Na) buffer 5 mM pH=6.8,
preparation of a freshly prepared solution of biotin BMCC (533.69 g/mole) at 8.5 mM (4.54 g/l) in DMSO,
preparation of a freshly prepared mixture of compound of example 1 (3618.26 g/mole) containing 2.5 mg/ml of deionised water, coupling to Fab' at the rate of 5 moles biotin BMCC or compound of example 1 per mole of Fab' (46,000 Daltons), incubation for 2 hours at laboratory temperature with rotary stirring in a brown glass bottle, blockage by addition of equimolar iodoacetamide to the biotin BMCC or to the compound of example 1, use of a freshly prepared solution of 10 mM iodoacetamide in PBS buffer, incubation for 1 h at laboratory temperature with rotary stirring, dialysis against PBS buffer+azide, exit from dialysis and determination of the concentration of the conjugates by measurement of OD at 280 nm (E=1.48)

4.4. Coupling of the Compound of Example 1 onto Antibodies Modified by Traut's Reagent The conjugates were obtained by coupling as follows:

modification of the antibody by addition of 20 moles of Traut's reagent for one mole of antibody, then dialysis in $PO_4$ 50 mM+NaCl 150 mM+EDTA(4Na) 5 mM buffer, pH=6.8, preparation of a freshly prepared solution of compound of example 1 (3618.26 g/mole) at 2.5 mg/ml in deionised water, coupling to the modified antibody at the rate of 20 moles of compound of example 1 per mole of antibody (160,000 Daltons), incubation for 2 hours at laboratory temperature with rotary stirring in a brown glass bottle, blockage by addition of equimolar iodoacetamide to the compound of example 1, use of a freshly prepared solution of iodoacetamide in PBS, incubation for 1 h at laboratory temperature with rotary stirring, dialysis against PBS buffer+azide, exit from dialysis and determination of the conjugate concentration by measurement of the OD at 280 nm (E=1.4)

4.5. Coupling of the Compound of Example 1 on Antigens Modified by Traut's Reagent The conjugates were obtained by coupling as follows:

modification of the antigen by addition of 4 moles of Traut's reagent for 1 mole of antigen, then dialysis in $PO_4$ 50 mM+NaCl 150 mM+EDTA(4Na) 5 mM buffer, pH=6.8, preparation of a freshly prepared solution of compound of example 1 (3618.26 g/mole) at 1 mg/ml in deionised water, coupling to the modified antigen at the rate of 1 moles of compound of example 1 per mole of antigen (MW=25,000 Daltons), incubation for 2 hours at laboratory temperature with rotary stirring in a brown glass bottle, blockage by addition of equimolar iodoacetamide to the compound of example 1, use of a freshly prepared solution of iodoacetamide in PBS, incubation for 1 h at laboratory temperature with rotary stirring, dialysis against PBS buffer+azide+SDS (sodium dodecylsulphate), exit from dialysis and determination of the concentration of the conjugates by measurement of the OD at 280 nm.

4.6. Coupling of Biotin NHs onto Antigens or Antibodies

The conjugates were obtained by coupling as follows:

dialysis of the antibodies or antigens in 0.1M $NaHCO_3$ buffer pH=8.3 preparation of a freshly prepared solution of biotin NHs at 11.36 g/l in DMSO for coupling the antibodies and a solution of 2.0 g/l in DMSO for coupling the antigens coupling to the antibody at the rate of 20 moles of biotin NHs per mole of antibody (160,000 Daltons), and coupling to the antigen at the rate of 1 mole biotin NHs per mole of antigen (25,000 Daltons)

incubation for 1 hour at ambient temperature with rotary stirring in a brown glass bottle, blockage by addition of equimolar 1M lysine pH=8.0 to the biotin NHs, incubation for 1 h at ambient temperature with rotary stirring, dialysis against PBS buffer+azide for the antibodies and in PBS+azide+SDS for the antigens, exit from dialysis and determination of the conjugate concentration by measurement of OD at 280 nm.

4.7. Coupling of the Compound of Example 1 and Biotin BMCC onto Antigens Reduced with DTT The conjugates were obtained by coupling as follows:

reduction of the antigen by addition of 800 moles of DTT per mole of antigen and stirring for 30 min at laboratory temperature, desalting of the reduced antigen on Sephadex G25 gel in PBS buffer+EDTA pH=7.5, preparation of a freshly prepared solution of biotin BMCC (533.69 g/mole) at 4.35 mM (2.32 g/l) in DMSO, preparation of a freshly prepared solution of the compound of example 1 (3618.26 g/mole) at 2.5 mg/ml in deionised water, coupling to the reduced antigen at the rate of 20 moles of biotin BMCC or of the compound of example 1 per mole of antigen (160,000 Daltons), incubation for 2 hours at laboratory temperature with stirring on vortex in a brown glass bottle, blockage by addition of 20 moles of NEM per mole of antigen, use of a freshly prepared solution of 10 mM of NEM in PBS buffer, dialysis of the conjugates in PBS+MIT, exit from dialysis.

EXAMPLE 5

Application to ELISA Direct and Indirect Detection Tests 5.1. Direct ELISA Test

The activity of the conjugates comprising a tetrabiotinylated compound of the invention or a single biotin is compared with a direct ELISA test, by fixing the conjugates onto microplate and by developing the signal by means of streptavidin coupled to peroxidase. This test serves to compare the "coupling level" of the polybiotinylated compounds, according to an embodiment of the invention, with monobiotinylated compounds.

Protocol:

Use of Maxisorp well strips (for deposition of antibody fragments and whole antibodies) or Polysorp well strips (for deposition of antigens).

Dilution of the monobiotinylated or tetrabiotinylated conjugates between 0.05 µg/ml and 0.5 µg/ml in 50 mM $CO_3$ buffer pH=9.6, followed by twofold dilutions.

Deposition of 100 µl/well of each dilution

Incubation overnight at laboratory temperature 3 washings in PBS tween

Deposition of 100 µl/well of streptavidin-peroxidase diluted to 1/60000 in PBS

Incubation for 15 min in the oven at 37° C.

3 washings in PBS tween

Deposition of 100 µl/well OPD

Incubation for 30 min in darkness at laboratory temperature

Blockage with 100 µl/well 1.8$NH_2SO_4$

Reading of the OD at 492 nm 5.2. Indirect ELISA Test with an Anti-Salmonella Fab' Conjugate/Tetrabiotinylated or Monobiotinylated Compound For this purpose, the antigens issuing from the culture of the three strains of *Salmonella* were coated on Polysorp microplates. The following steps were then carried out:

Passivation for 1 h in the oven at 37° C. with 1 g/l BSA in PBS, 3 washings with PBS tween, then Incubation of the conjugates diluted twofold in PBS for 30 min at 37° C., 3 washings with PBS tween.

The same procedure was then followed as in the direct ELISA test from the deposition of streptavidin.

The indirect ELISA serves both to test the "coupling level" and the biological reaction between the conjugate and the antigen or the antibody.

5.3 Results

The results are shown in FIGS. 2 to 8 as follows:

FIG. 2 is the graphic representation giving the OD results of the direct ELISA test of the anti-*Listeria monocytogenes* (LMO) Fab' conjugate that is monobiotinylated (by biotin BMCC) or tetrabiotinylated (by a compound according to an embodiment of the invention), fixed to the bottom of the microplate, according to its concentration, FIG. 3 is the graphic representation giving the OD results of the direct ELISA test of the anti-Salmonella Fab' conjugate that is monobiotinylated (by biotin BMCC) or tetrabiotinylated (by a compound according to an embodiment of the invention), fixed to the bottom of the microplate, according to their concentration, and of the indirect ELISA test of these same conjugates, but detected by means of *Salmonella* antigens, FIG. 4 is the graphic representation giving the OD results of the direct ELISA test of two anti-HIV Fab' conjugates that are monobiotinylated (by biotin BMCC) or tetrabiotinylated (by a compound according to an embodiment of the invention), fixed to the bottom of the microplate, according to their concentration, FIG. 5 is the graphic representation giving the OD results of the direct ELISA test of the anti-Kallikrein Fab' conjugate that is monobiotinylated (by biotin BMCC) or tetrabiotinylated (by a compound according to an embodiment of the invention), fixed to the bottom of the microplate, according to its concentration, FIG. 6 is the graphic representation giving the OD results of the direct ELISA test of the gp160 antigen conjugate reduced with DTT that is monobiotinylated (by biotin BMCC) or tetrabiotinylated (by a compound according to an embodiment of the invention), fixed to the bottom of a microplate, according to its concentration, FIG. 7 is the graphic representation giving the OD results of the direct ELISA test of surface antigen conjugates of hepatitis B that are monobiotinylated (by biotin NHs) or tetrabiotinylated (by a compound according to an embodiment of the invention), fixed to the bottom of the microplate, according to their concentration, and FIG. 8 is the graphic representation giving the OD results of the direct ELISA test of the anti-Salmonella antibody conjugate that is monobiotinylated (by biotin NHs) or tetrabiotinylated (by a compound according to an embodiment of the invention), fixed to the bottom of the microplate, according to its concentration.

The results demonstrate a significant improvement of the signal using the polybiotinylated molecule according to the invention, despite its hindrance. In particular, for OD of 1.8, gains can be observed such as given in Table 6 below:

TABLE 6

|  | Biotin BMCC | Biotin NHs | Tetrabiotin | Signal gain |
|---|---|---|---|---|
| LMO Test 1 | 46 ng/ml | NA | 6 ng/ml | × 8 |
| LMO Test 2 | 6.0 ng/ml | NA | 0.4 ng/ml | × 15 |
| HIV Antibody A | 0.078 µg/ml | NA | <0.0078 µg/ml OD = 1.895 | > × 10 |
| HIV Antibody B | 0.08 µg/ml | NA | <0.0078 µg/ml OD = 2.021 | > × 10 |
| Kallikrein | 0.287 µg/ml | NA | <0.0023 µg/ml OD = 2.226 | > × 124 |
| Salmonella Fab' direct ELISA | 0.012 µg/ml | NA | <0.0039 µg/ml OD = 2.825 | > × 30 |
| Salmonella Fab' indirect ELISA | 0.226 µg/ml | NA | 0.101 µg/ml | × 2.2 |
| Antigen GP160 reduced with DTT | 0.01 µg/ml | NA | <0.0039 µg/ml OD = 2.813 | > × 2.5 |
| Antigen HBs Ad | NA | 5 µg/ml OD = 1.320 | Traut (1/4) Tetrabiotin (1/1) 0.063 µg/ml | < × 79 |
| Antigen HBs Ay | NA | 2.27 µg/ml | Traut (1/4) Tetrabiotin (1/1) 0.046 µg/ml | × 49 |
| Salmonella antibody | NA | (1/20) 0.19 µg/ml | Traut (1/20) Tetrabiotin (1/20) 0.029 µg/ml | × 6.5 |

EXAMPLE 6

Application to Diagnostic Tests with Strains of *Listeria*

The purpose of this test is to compare the Vidas signal obtained between a tetrabiotinylated conjugate according to an embodiment and a monobiotinylated conjugate, in order to increase the sensitivity of the response without degrading the specificity.

6.1 Materials and Methods

Reagents Used

The tetrabiotinylated and monobiotinylated conjugates were prepared using a Fab' antibody fragment of *Listeria monocytogenes* (bioMérieux, France) and biotin BMCC and a compound as prepared in example 1, respectively, following the protocol described in section 4.3 above.

The other reagents are as follows:

LMO2 cones and well strips (bioMerieux, Reference 30 704)

PAL streptavidin (BioSPA, Ref: 045 66074)

Monobiotinylated stock solution: concentration 0.32 mg/ml of Fab'

Tetrabiotinylated stock solution: concentration 0.26 mg/ml of Fab'

LMO2 conjugate diluent (bioMerieux, Ref 500 26004)

PAL streptavidin diluent (bioMerieux, Ref 500 25992)

1 Vidas apparatus (bioMerieux)

Strains Tested

*Listeria monocytogenes* 4b ATCC 19115

*Listeria monocytogenes* 3a ATCC 51 782

*Listeria monocytogenes* 1/2c 83 09 024

*Listeria monocytogenes* 4c 83 09 031

*Listeria innocua* 6a 83 09 035

*Listeria ivanovii* 91 01 014

*Listeria welshimeri* 94 09 074

Methods

All the strains were cultured for 24 h at 37° C.±1° C. in LX Ref 42 120 broth, then heated for 5 minutes at 95-100° C.

The strains of *Listeria innocua, Listeria ivanovii* and *Listeria welshimeri* were used pure. These strains serve to test the specificity, because they are not recognised by the coupled antibody.

The four strains of *Listeria monocytogenes* were tested in dilution and were counted. These strains serve to test the sensitivity of the test.

The 2 conjugates were adjusted to the concentration of 0.36 µg/ml of Fab'.

To use the kit of the LMO2 well strip, the initial conjugate was withdrawn from the well X5. This well was rinsed with 600 µl of physiological water. Then, after having removed the physiological water, 400 µl of the monobiotinylated conjugate or of the tetrabiotinylated conjugate to be tested were added. 500 µl of sample (dilution of strains) were deposited in well X0 and the LMO2 Vidas test was started. The test lasts about 80 minutes.

Results

The results are given in Table 7 below.

TABLE 7

| Strains and count | Stock solutions | |
|---|---|---|
| | Tetrabiotinylated | Monobiotinylated |
| | RFV* | |
| L. mono 4b ATCC 19 115 1.5.10⁵ | 9957 | 9817 |
| L. mono 4b ATCC 19 115 1.5.10⁴ | 4350 | 2285 |
| L. mono 4b ATCC 19 115 1.5.10³ | 199 | 233 |
| L. mono 3a ATCC 51 782 1.6.10⁵ | 8517 | 6958 |
| L. mono 3a ATCC 51 782 1.6.10⁴ | 1612 | 829 |
| L. mono 3a ATCC 51 782 1.6.10³ | 160 | 78 |
| L. mono 1/2c 83 09 024 2.1.10⁵ | 9806 | 8779 |
| L. mono 1/2c 83 09 024 2.1.10⁴ | 2880 | 1472 |
| L. mono 1/2c 83 09 024 2.1.10³ | 309 | 151 |
| L. mono 4c 83 09 031 8.4.10⁴ | 2413 | 1427 |
| L. mono 4c 83 09 031 8.4.10³ | 143 | 82 |
| L. mono 4c 83 09 031 8.4.10² | 19 | 10 |
| L innocua 6a 83 09 035 | 7 | 9 |
| L ivanovii 91 01 014 | 7 | 3 |
| L welshimeri 94 09 074 | 10 | 6 |

*Relative Fluorescent Value

The results in the table above show that the use of a conjugate having a tetrabiotinylated compound according to an embodiment of the invention serves to double the signal, and hence to increase the sensitivity of the test. At the same time, its use does not alter the specificity, because in this case, the signals are identical.

The invention claimed is:

1. Method for preparing a compound having the formula (I):

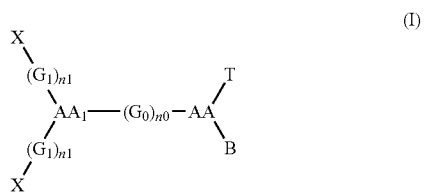

wherein

X is biotin or

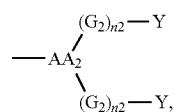

Y is biotin or

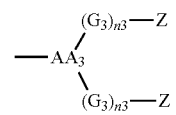

Z is biotin or

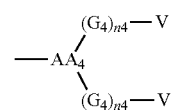

V is biotin or

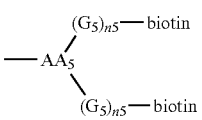

B is $NH_2$ or H,

AA is a trifunctional molecule derivative when B is $NH_2$ or a bifunctional molecule derivative when B is H, $AA_1$ to $AA_5$ are each independently a trifunctional molecule derivative, $G_0$ to $G_5$ are each independently an arm comprising at least one ($-CH_2-CH_2-O$) unit, $n_0$ to $n_5$ are each independently a whole number between 1 and 8 and T is an antiligand or a reactive group for fixation to an antiligand, said antiligand being capable of reacting with a ligand, the method comprising:

(i) grafting $n_0$ compounds having the formula $W''_0$-$G_0$-OH, where $W''_0$ is an amine protecting group, $n_0$ and $G_0$ being such as defined above, to a compound having the formula (II):

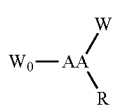
(II)

where R is a prefunctionalised resin, W and $W_0$ are different from one another and represent an amine protecting group, W being different from $W''_0$, and AA is such as defined above, to obtain a compound having the formula (III):

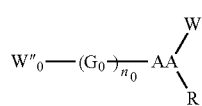
(III)

(ii) coupling a compound having a formula (IV):

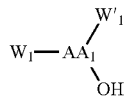
(IV)

where $W_1$ and $W'_1$ are amine protecting groups that are identical to or different from one another and from the $W_0$ and $W''_0$ groups, but different from W, and $AA_1$ is such as defined above, with the compound having the formula (III) to obtain a compound having the formula (V):

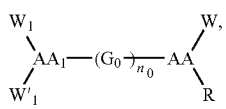
(V)

(iii) grafting $2n_1$ compounds having the formula $W''_1$-$G_1$-OH, where $W''_1$ is an amine protecting group, identical to or different from one another and from the other protecting groups used in this method, but different from W, $G_1$ and $n_1$ being such as defined above, onto the compound obtained in step (ii) to obtain a compound having the formula (VI):

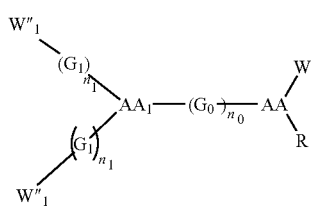
(VI)

(iv) when X in the formula (I) is biotin, passing directly to step (v); if not, when X in the formula (I) is not biotin, repeating the steps (ii) and (iii) with $2^{p-1}$ compounds having the formula (VII):

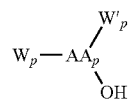

and $2^p n_p$ times the compound having the formula $W''_p$-$G_p$-OH, where p is a whole number between 2 and 5, and $W_p$, $W'_p$, $W''_p$ are amine protecting groups that are identical to or different from one another and from the other protecting groups used in this method, but different from W, and $AA_p$ is a trifunctional molecule, according to the following sequence:

1 time when Y is biotin, p then being equal to 2

2 times when Y is not biotin and Z is biotin, p then being equal to 2 then to 3, 3 times when Y and Z are not biotin and V is biotin, p then being equal to 2, 3 then 4, and 4 times when Y, Z and V are not biotin, p then being equal to 2, 3, 4 then 5, (v) deprotecting the compound thus obtained at the $W''_1$ or $W''_p$ group, p being between 2 and 5, and coupling with biotin, (vi) deprotecting, at the W group, the compound thus polybiotinylated and coupling with an antiligand or a reactive group for fixation to an antiligand (T) and (vii) cutting the compound thus obtained from the resin (R) to obtain a compound having the formula (I).

2. Method according to claim 1, wherein the substituents $AA_1$ and $AA_2$, if applicable $AA_3$, $AA_4$ and $AA_5$, are identical and are preferably a lysine derivative.

3. Method according to claim 1, wherein the substituents $G_0$, $G_1$, if applicable $G_2$, $G_3$, $G_4$ and $G_5$ are identical and preferably have the formula (—NH—$CH_2$—$CH_2$—O—$CH_2$—$CH_2$—O—$CH_2$—CO—).

4. Method according to claim 1, wherein the whole numbers $n_0$, $n_1$, if applicable $n_2$, $n_3$, $n_4$ and $n_5$, are identical and are preferably equal to 2 or 3.

5. Method according to claim 1, wherein the W group is methoxytrityl.

6. Method according to claim 1, wherein $W_1$ and $W'_1$ are identical and, if applicable, $W_2$ and $W'_2$ are identical, $W_3$ and $W'_3$ are identical, $W_4$ and $W'_4$ are identical and $W_5$ and $W'_5$ are identical.

7. Method according to claim 6, wherein the amine protecting groups $W_1$, $W'_1$ and, if applicable, $W_2$, $W'_2$, $W_3$, $W'_3$, $W_4$ and $W'_4$, $W_5$ and $W'_5$ are fluorenylmethoxycarbonyl groups.

8. Method according to claim 1, wherein the substituent AA is a lysine derivative and B is $NH_2$.

9. Method according to claim 1, wherein X is

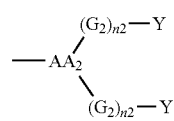

and Y is biotin.

* * * * *